United States Patent
Dealy et al.

Patent Number: 5,094,100
Date of Patent: Mar. 10, 1992

[54] METHOD AND APPARATUS FOR MEASURING SHEAR STRESS

[76] Inventors: John M. Dealy, 315 Roslyn Avenue, Westmount, Quebec, Canada, H3Z 2L7; Shailesh R. Doshi, 523 Portsmouth, Apt. 601, Kingston, Ontario, Canada, K7M 7H6; Frank R. Bubic, 5140 MacDonald, Suite 1602, Montreal, Quebec, Canada, H3X 3Z1

[21] Appl. No.: 551,007

[22] Filed: Jul. 11, 1990

[51] Int. Cl.⁵ .............................. G01N 11/02
[52] U.S. Cl. .............................. 73/54; 73/59
[58] Field of Search .......... 73/59, 60, 54, 64.1, 73/841, 861.71, 861.74

[56] References Cited

U.S. PATENT DOCUMENTS

| | | | |
|---|---|---|---|
| 3,525,252 | 8/1970 | Kocatas | 73/54 |
| 4,062,226 | 12/1977 | Hietala | 73/63 |
| 4,757,708 | 7/1988 | Hietaranta | 73/59 |

FOREIGN PATENT DOCUMENTS 0015838  1/1984  Japan ........................... 73/59

Primary Examiner—Hezron E. Williams
Assistant Examiner—Shu-Cheng Kau
Attorney, Agent, or Firm—Watson, Cole, Grindle & Watson

[57] ABSTRACT

There is provided an apparatus for measuring the shear stress of a fluid wherein the shear stress is determined by measuring the movement of one end of a substantially rigid lever with the other end having the active face forming the shear stress measurement surface.

14 Claims, 3 Drawing Sheets

METHOD AND APPARATUS FOR MEASURING SHEAR STRESS

BACKGROUND OF THE INVENTION

The present invention relates to a method and apparatus for measuring shear stress and in particular, the invention relates to an improved shear stress transducer for use with viscous or viscoelastic fluids.

Shear stress transducers that measure the shear stress exerted on a solid surface by a viscous or viscoelastic fluid are known in the art and thus, reference may be had to U.S. Pat. No. 4,464,928 issued Aug. 14, 1984 to John M. Dealy which teaches a method and associated apparatus for the measurement of shear stress. A method and apparatus for the measurement of rheological properties involving the use of a shear stress transducer is the subject of U.S. Pat. No. 4,571,989 issued Feb. 25, 1986 to John M. Dealy.

In one of the embodiments described in U.S. Pat. No. 4,464,928 the shear stress is determined by measuring the deflection of an elastic beam, where the beam is rigidly fixed at one end with the shear sensitive surface, which we will call the active face, forming tee opposite end. This is a cantilever configuration in which the lateral load (the shear force to be measured) is applied to one end while the other is fixed. This embodiment has the advantages that it is simple to manufacture and robust However, since the maximum deflection of the beam occurs at the active face, in order to optimize the sensitivity of the device it is necessary to measure the deflection as closely as possible to this end.

This may interfere with its installation in a rheometer, flow channel or processing machine. Furthermore, if the fluid of interest is under pressure, it will flow into the shear stress transducer. One way of preventing this, which was mentioned in the teaching of the aforementioned earlier patents, is to install an elastomeric seal around the active face of the beam. This can be a premolded seal, similar to an "O" ring, or a cured-in-place elastomer such as a silicone rubber. In either case, however, there will be a limit on the pressure that can be withstood without dislodging the seal or otherwise interfering with the measurement of the shear stress. This limit may be as low as 2,000 psi. Since industrial processes often involve pressures considerably higher than this, this limits the application of the shear stress transducer in industrial manufacturing operations.

SUMMARY OF THE INVENTION

It is therefore an object of the present invention, to provide a shear stress transducer where the measurement of deflection is away from the active face, and wherein higher pressures can be tolerated without interfering with the performance of the shear stress transducer.

Generally, according to one embodiment of the invention, there is provided an apparatus for measuring the shear force acting on a portion of a solid surface, the apparatus comprising a lever having an active arm and a reactive arm connected by a center portion which is secured to a housing at least partially surrounding the lever, the active arm having an end thereof forming the shear sensing face, and the reactive arm having means associated therewith to detect and measure movement thereof.

The apparatus and method of the present invention is particularly suitable for measuring the local shear stress exerted by flowing liquid on the surface of a wall bounding the flow. The practice of the present invention is particularly suitable for measuring shear stress in viscous or viscoelastic liquids such as polymer solutions and melts. The apparatus and method may conveniently be used to measure shear stresses in liquids having viscosities between about $10^2$ and about $10^{11}$ centipoise.

The rigid lever is preferably of a unitary construction along with the elastic portion which connects the lever to the housing. For use, the active arm is preferably mounted with the measuring face being positioned flush with the surface on which the shear stress is to be measured. The elastic portion forming the connection between the lever and the housing is preferably the only portion which deforms under load with the active arm being formed to be sufficiently rigid so as not to bend significantly under any applied shear force.

There are many different design consideratons which must be taken into account to optimize functioning of the device. In order to increase sensitivity, several design parameters must be taken into consideration.

The quantity actually measured is the lateral displacement of the reactive face, $x_r$, while the quantity of interest is the shear stress, $\sigma$, acting on the active face. For a static stress, the relationship between these two quantities for a rigid lever is:

$x_r = \sigma A L_a L_r / K$

A = area of active face
$L_a$ = length of active lever arm
$L_r$ = length of reactive lever arm
K = torsional modulus of elastic member In order to maximize this quantity for a given shear stress, it is clearly advantageous that $L_a = L_r$, that K be small, and that $(L_a + L_r)$ and A be large. However, this may conflict with other design considerations described below, and the final design must represent a compromise optimized for a particular application.

Apart from the above, it is desirable to minimize the lateral deflection of the active face for several reasons. First, the gap around the active face should be small so that there is a minimum influence of the shear stress transducer on the flow and deformation of the fluid in its vicinity. Secondly, for dynamic measurements, if there is fluid in the gap it will damp the response of the transducer leading to a deterioration of its frequency response, the smaller the lateral deflection of the face, the smaller the effect of this damping. Thirdly, if an elastomeric seal is used to prevent the ingress of fluid into the gap, it is desirable that this seal act as a linear elastic element, and this type of response will be most likely when the deformation of the elastomer is very small.

For a rigid lever the lateral deflection of the active face, $x_a$, is $X_a = x_r L_a / L_r$ This implies that in order to minimize $x_a$ for a given $x_r$, it is desirable that $L_r/L_a$ be large. This is inconsistent with the criterion for maximizing the sensitivity. However, because of the mathematical form of the sensitivity criterion there is only a small penalty in sensitivity for modest increases in $L_r/L_a$. For example, for $L_r/L_a = 1.5$, the loss in sensitivity is only 4%, while the reduction in $x_a$ for a given $x_r$ is 50%. Further improvement by increasing $L_r/L_a$ is theoretically possible, but mechanical design problems may arise for values much greater than 1.5. Thus, it is preferred that the ratio of the lengths of the reactive arm range between 1:1 and 2:1.

The transducer will often be used in an environment in which there is mechanical vibration, and this can result in a noisy transducer output due to vibration of the lever relative to the transducer body to which the proximity sensor is attached or of the body relative to the lever. To eliminate vibrations excited by lateral motions of the transducer, the center of gravity of the lever should be on the axis of the lever at the location of the elastic member that couples it to the body. A remaining possible mode of vibration is rotation of the lever about an axis that is perpendicular to itself and at the location of the elastic member. For an undamped system, the resonant frequency for this motion is $\sqrt{K/I}$, where K is the elastic modulus of the elastic member, and I is the moment of inertia of the lever. The latter quantity is related to the mass and geometry of the lever. If the transducer is designed in such a way that this frequency is much higher than those of the exciting motions, the resulting noise in the output signal will be minimized. To maximize the resonant frequency, K should be large, while the mass and total length should be small.

Another possible source of excitation for induced lever vibration is a fluctuation in the stress that is being measured. In order to avoid such an excitation, it is desirable that the frequency of the stress variation be much less than the resonant frequency of the lever. Another advantage of this arrangement is that if there are environmentally excited vibrations in the neighborhood of the resonant frequency, the output signal can be easily filtered to eliminate these with minimal effect on the measurement of the stress as a function of time.

In an unpressurized installation, for example in a laboratory rheometer, some of the fluid to which the active face is exposed may enter the gap surrounding this face due to a positive first normal stress difference of the fluid or to a squeezing flow normal to the plane of the active face. Such a squeezing flow might, for example, result from the assembly of a sliding plate rheometer after sample insertion. In a pressurized installation, for example when the transducer is being used to monitor the state of a fluid while it is being processed, fluid will enter the gap under the influence of hydrostatic pressure unless the transducer is sealed, for example by an elastomeric material in the gap.

Whenever there is a fluid in the gap, it will affect the response of the transducer. As long as the fluid does not gel or become rigid, for example due to drying or cross-linking, the effect will be only to damp the dynamic response of the transducer and there will be no effect on the steady state measurements. An approximate analysis of the effect of a Newtonian fluid on the dynamic response of the transducer can be used to determine the principal effects of this damping. We consider for simplicity of analysis an active face that is a rectangle. The shear force acts on the X-Y face in the X direction, while Z is the thickness of the face. Let the gap surrounding the face be $b_o$ when $F=0$. An approximate damping flow analysis shows that, for small displacements ($X_a = b - b_o$) of the active face in the X direction, the gap, b, will change with time in response to a suddenly imposed shear force, F, as follows:

$$b(t) = b_o + (b_1 - b_o)(1 - e^{-t/\lambda})$$

where $b_1 - b_0$ = equilibrium displacement for force F $$\lambda = \frac{2\eta S}{\sqrt{A}} \left[ \left(\frac{Z}{b_o}\right) \frac{X}{\sqrt{Y}} + \left(\frac{Z}{b_o}\right)^3 \frac{1}{\sqrt{X/Y}} \right]$$

Z = thickness of active face
n = viscosity of fluid
S = $(b_1 - b_9)XY/F$

The quantity S is the primary sensitivity, defined as the amount of deflection of the active face divided by the applied shear stress. The first term in the brackets in the definition of $\lambda$ is due to shearing of the fluid in the gaps that are slits parallel to the X direction, while the second term is due to compression and tension in the gaps that are slits parallel to the Y direction. Clearly when $Z \geq b_o$, the compression and tension at the ends make the most important contributions.

For a sinusoidal shear stress acting on the active face, the result of the damping on the deflection of the lever is an attenuation in the amount of $1/[1+(\lambda\omega)^2]$ and a phase lead of arctan ($\lambda\omega$). It is obviously advantageous that $\lambda\omega$ be small. For example, when $\lambda\omega = 0.1$, the attenuation will be 0.995, while the phase shift will be 0.1 radian.

To minimize the damping, i.e., for the best dynamic response, it is clearly advantageous, for a given viscosity, to have:
1. maximum area of the active face
2. minimum thickness of the active face, Z
3. maximum gap, $b_o$
4. maximum length to width ratio X/Y However, other considerations lead to contradictory requirements. The area should not be too large in order to reduce the size of the transducer and to produce a measured value characteristic of the shear stress over a small area. The gap should be kept small to minimize any disturbance in the flow or deformation of the fluid in the neighborhood of the surface in which the transducer is mounted. Also, a long thin active face (Y<<X) can be difficult to fabricate. The simplest shape to fabricate is a circle, and the damping time for this shape will be approximately equal to that for a square (X = Y). Thus, for a given shape and area of the active face, the only design parameters are $b_o$ and Z. A design that has been found to yield satisfactory results for molten polymers is one in which the active face is circular and the active arm has the shape shown in FIG. 5. In this way, the gap seen by the fluid is small while the effective gap for the damping motion is large and the squeezing area is small. An optimal shape from this point of view is one in which the active face and surrounding end of the housing have sharp corners, with the disadvantage that this would produce a fragile face that could be easily damaged.

If an elastomeric seal is used to prevent fluid from entering the transducer, its viscoelastic properties will influence the dynamic response of the transducer. If the elastomer acts as a linear elastic member (storage modulus constant and loss modulus zero), its only effect will be to increase the effective rigidity of the transducer. However, if it is viscoelastic, then its contribution to the spring constant will be frequency dependent, and there will also be a frequency-dependent damping effect. The elastomer should be selected so that within the range of frequencies expected in the stress as a function of time, it is in its plateau region.

Having thus generally described the invention, reference will now be made to the accompanying drawings, in which:

DETAILED DESCRIPTION OF PREFERRED EMBODIMENTS

Figure 1:
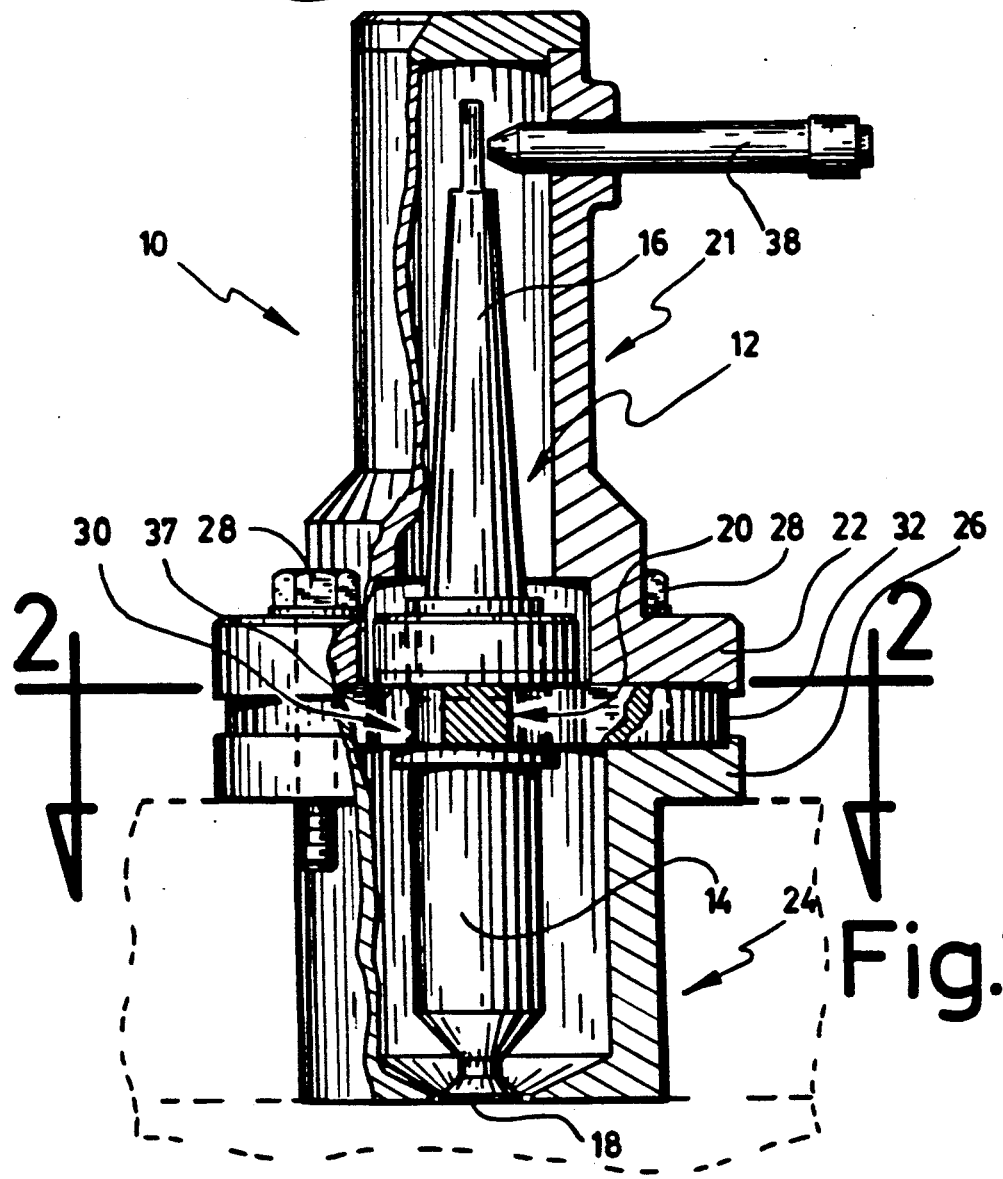
FIG. 1 is a side cut away view partially in section, of an embodiment of a shear stress transducer.

Referring to the drawings in greater detail and by reference numerals thereto, FIG. 1 illustrates one embodiment of a shear stress transducer according to the present invention.

Transducer 10 comprises a rigid lever 12 which is made of suitable material having the desired properties of rigidity and lightness. Typically, it is formed of a metallic material and can be manufactured as a one piece unit. Lever 12 has an active arm 14 and a reactive arm 16. Active arm 14 has an active face 18 which is exposed to the material whose shear stress is being measured. As discussed, it is often desirable to make active face 18 as small as possible so that the measured force divided by the area corresponds to the shear stress acting over a small neighborhood of a specific point. If made too small, however, as the shear force becomes small it becomes more difficult to measure. Furthermore, the role of the squeezing of the flow of the material in the gap increases relative to the shear force. In the illustrated embodiment, a circular surface with a diameter of between 0.6 to 1.0 cm has been found to be suitable for use with molten polymers.

A first housing member 21 surrounds reactive arm 16 and includes a flange 22 extending exteriorily thereof. A second housing member 24 extends about active arm 14; one end thereof is in close proximity to active face 18 as will be described in greater detail hereinbelow while at the other end there is provided a flange generally designated by reference numeral 26. Housing members 21 and 24 are joined together by means of bolts 28 through flanges 22 and 26 to substantially enclose and hold lever 12 as will be described.

Figure 2:
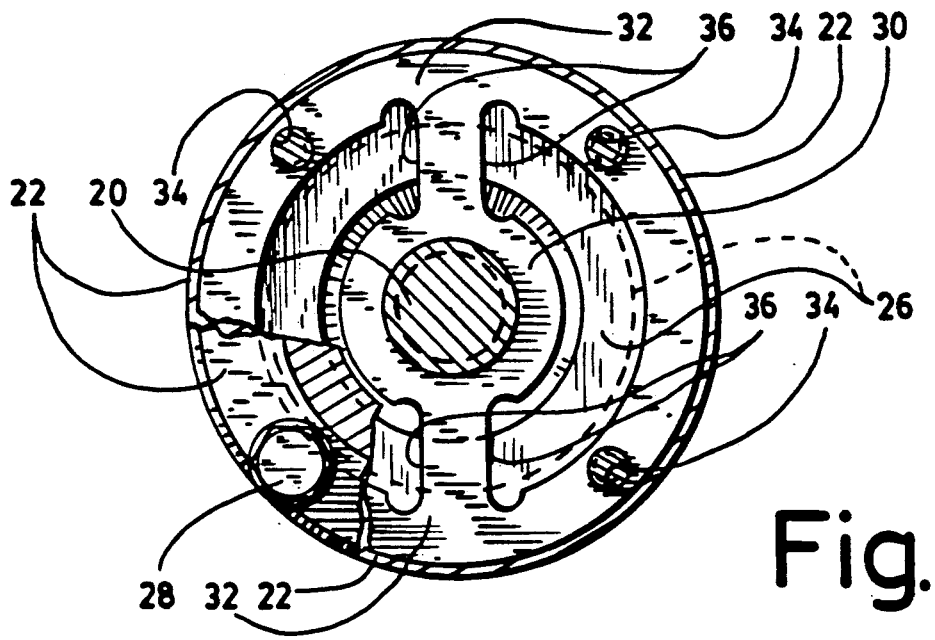
FIG. 2 is a cross sectional view taken along the line 2—2 of FIG. 1.

Lever 12, between active arm 14 and reactive arm 16 has a center section 20. As previously discussed, active arm 14 is designed to be very rigid so that it does not bend significantly under the applied shear force. The transducer functions on the basis that forces are transmitted from the active arm to the reactive arm by means of an elastic element which connects center section 20 with housing members 21 and 24. This may be best illustrated by referring to FIG. 2 which illustrated the elastic element designated generally be reference numeral 36. Elastic element 36 is an integral part of the slotted disk shown in FIG. 2 which consists of an inner ring 30 and an outer ring 32. Inner ring 30 and outer ring 32 are connected by means of a pair of torsion bars which act as the elastic element in this embodiment. The slotted disk is rigidly clamped to the lever 12 by means of a nut 37 that bears on the inner ring 30.

In the embodiment of FIG. 1 wherein torsion bars 36 link inner ring 30 and outer ring 32, the disk unit can be made from a single disc of metal or other appropriate rigid material by cutting or machining or molding appropriate slots in the disc. By proper selection of the thickness of this disc relative to the width of the torsion bars 36, the compliances of the bars in torsion (in response to a shearing force on the active face) and in shear (in response to an axial force on the active face) can be independently fixed.

The transducer is assembled such that outer ring 32 is held in position by clamping between flanges 22 and 26 of housing members 21 and 24 respectively. Bolts 28 pass through apertures 34 in outer ring 32.

At the free end of reactive arm 16 a proximity probe 38 is positioned. Proximity probe 38 will detect the distance between its end and the free end of reactive arm 16. For most types of proximity probes, it would be desirable to make the surface of the free end of reactive arm 16 as flat as possible with its plane containing the axis of lever 12 and perpendicular to the axis of proximity probe 38.

Figures 5, 6:
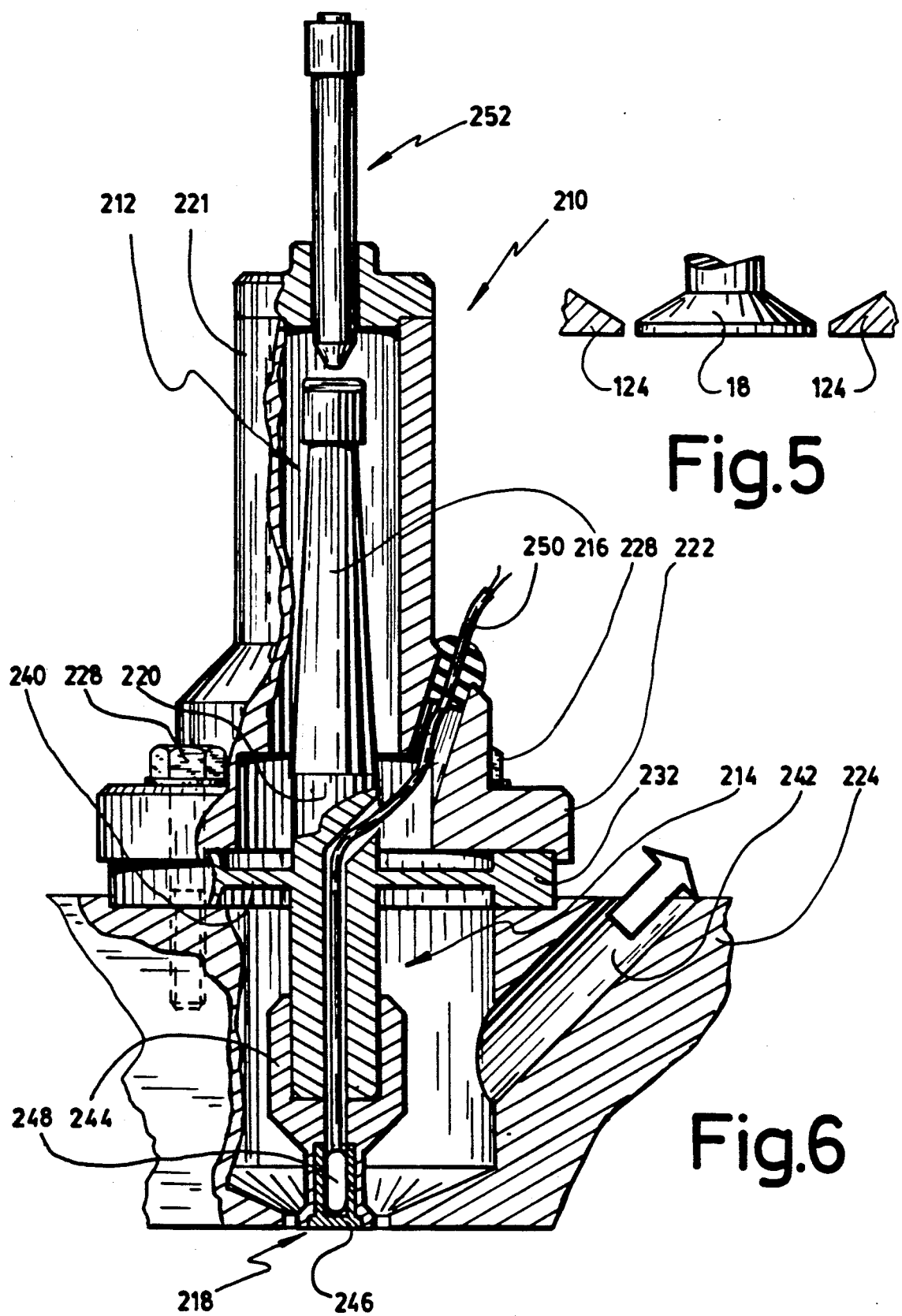
FIG. 5 is a detail view of one embodiment of an active face of the shear stress transducer.
FIG. 6 is a cut-away view, partially in section, of a further embodiment of a shear stress transducer.

FIG. 5 illustrates a typical active surface 18 on the active arm 14. As will be seen, second housing member 124 is machined to leave only a small gap with a relatively sharp edge.

Figure 4:
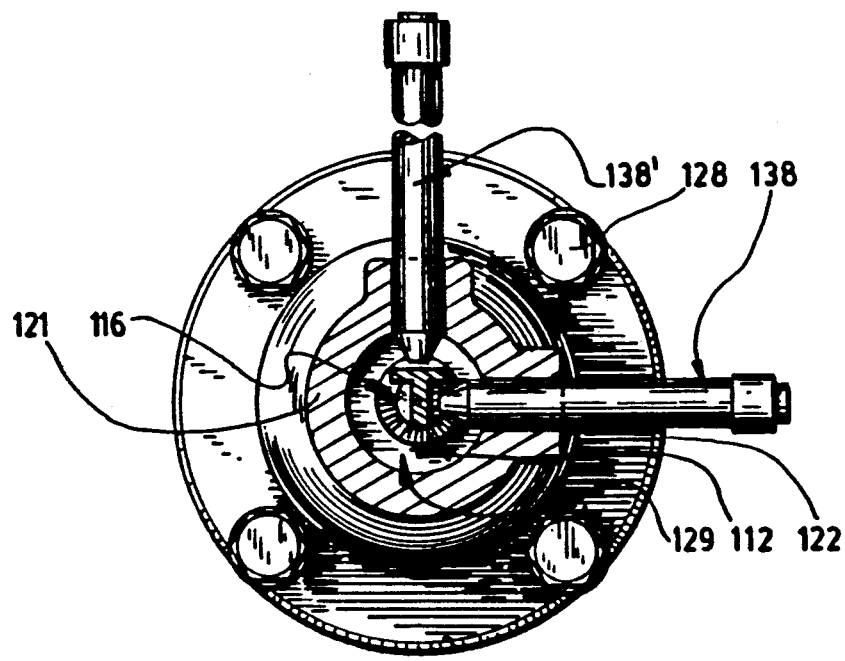
FIG. 4 is a cross sectional view taken along the line 4—4 of FIG. 3.
Figure 3:
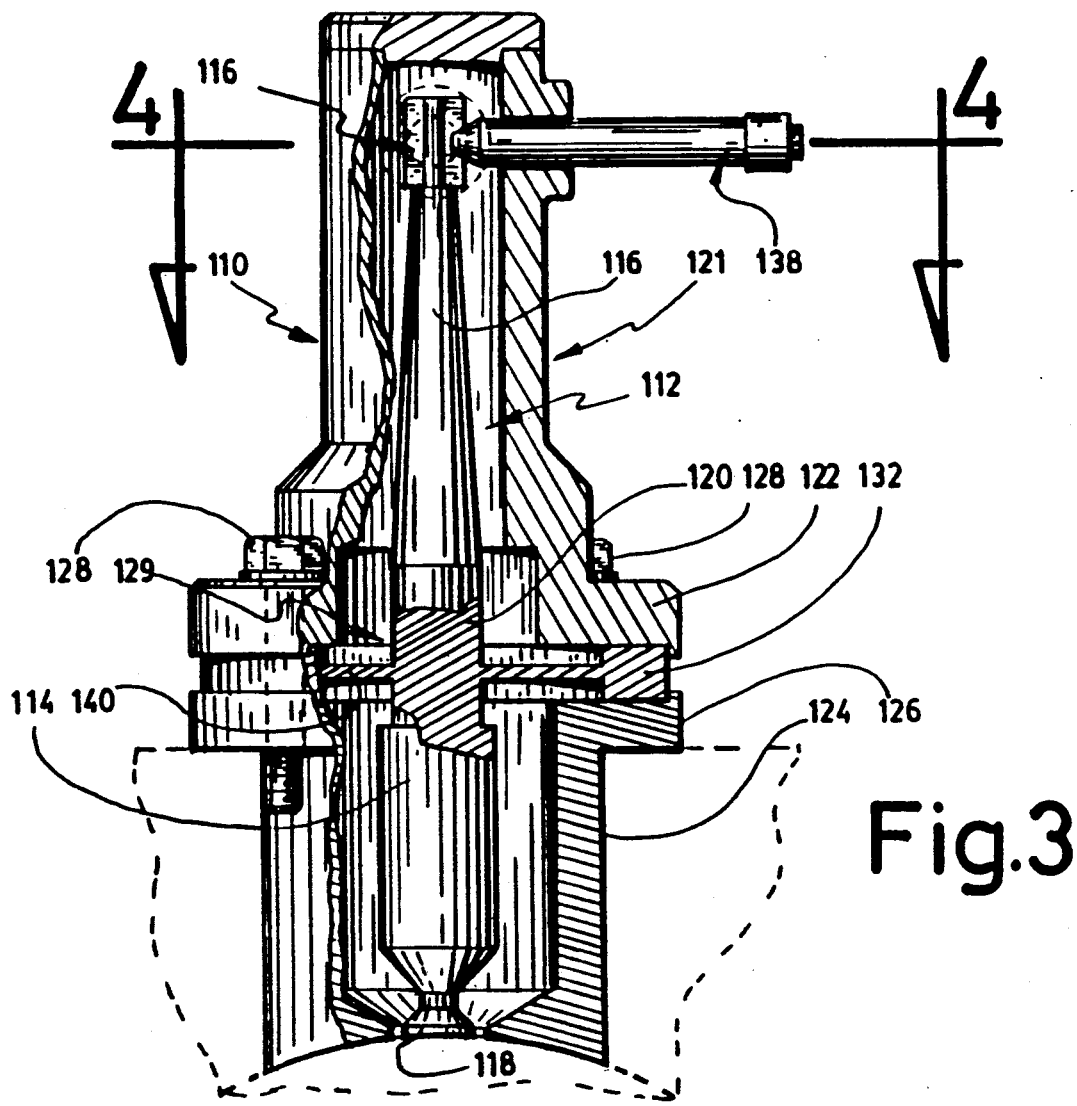
FIG. 3 is a cut-away view, partially in section of a further embodiment of a shear stress transducer according to the present invention.

A further embodiment of the apparatus of the present invention is illustrated in FIGS. 3 and 4 and reference will now be made thereto. In this embodiment, transducer 110 includes a lever 112 having an active arm 114 with active face 118 at the free end thereof. Center section 120 is intermediate active arm 114 and reactive arm 116. First and second housing members 121 and 124 have flanges 122 and 126 respectively, the housing members being held by means of bolts 128. In this embodiment, elastic portion 129 is formed of a solid diaphragm 140 extending between center portion 120 and an outer ring 132 clamped between the flange members 122 and 126. Diaphragm 140 will prevent any flow of fluid into the upper part of the transducer containing reactive arm 116 and thus prevent its interference with the means used to detect movement of the reactive arm. Accordingly, this embodiment is suitable for high pressure use.

In those cases where the fluid enters housing member 124, it will cause some damping of the dynamic response and will exert a force on the diaphragm in the axial direction. This force, as well as the normal force or pressure acting on the active face, must be taken into account in the design of the diaphragm. It is necessary to ensure that the axial deflection of the lever and of the active face is not sufficient to alter the flow geometry significantly. Another reason for keeping the axial deflection small is to ensure that the elastic response of the diaphragm will be linear so that its axial deflection will not affect its compliance in the warping mode of deformation associated with the rotation of the lever. It is also necessary to ensure that the total axial load is not sufficient to fracture the diaphragm. This is an important design consideration. In summary, the maximum axial load likely to be encountered must be estimated, and the diaphragm thickness and area must be specified accordingly.

As shown in FIG. 4, a pair of proximity probes 138 and 138' can be utilized so that one may measure not only the magnitude of the shear force, but the direction thereof. Using the two proximity probes, it is desirable to machine the two surfaces being measured as flat as possible in the appropriate planes as shown in FIG. 4. Active face 118 can be mounted in a curved surface and accordingly will have a curved active face as shown in FIG. 3. Such an installation can be useful in the measurement of shear stress exerted by a fluid or fluid-like material on the barrel of an extruder. The active face can be machined to match the curvature of this surface. In such an installation, the shear stress does not act over the entire surface of the active face in a direction normal to the axis of the lever, but the resulting error in the measured shear stress is very small as long as the diameter of the active face is much less than the radius of curvature of the surface in which it is mounted.

FIG. 6 illustrates a somewhat modified embodiment of the present invention and reference will now be made thereto. In this embodiment, transducer 210 comprises a lever 212 which has an active arm 214, a reactive arm 216 (described hereinbelow) with center section 220 connecting the active and reactive arms. An elastic diaphragm 240 (similar to FIG. 3) terminates in an outer ring 232. Bolts 228 extend through flange 222 of upper housing member 221 to secure the outer ring in position.

As shown in FIG. 6, a purge channel 242 may be provided to purge the fluid from the transducer body. This may be required because of thermal degradation or cross linking. Purge channel 242 may allow for continuous purge flow of fluid through the transducer. It is desirable that the magnitude of this flow be limited by the size of the purge channel 242 and/or a valve can be used to regulate this flow. Restricting the flow will, of course, increase the pressure and thus the total axial force on the diaphragm.

It is important to ensure that the purge flow does not compromise the reliability of the shear stress measurement. The flow will result in a drag force on the active arm of the lever and if the resultant force has a component in the direction of the applied shear force, it will result in a deflection of the lever such as to introduce an error into the shear stress measurement. This can be minimized by locating the purge channel at a position 90° away from the expected direction of the applied shear force to be measured. In operation, and to avoid large purge flows that will interfere with the shear stress measurement, one may purge intermittently at a higher rate, recognizing that the output of the transducer may not be an accurate indication of the shear stress during the high rate purging period.

Active arm 214 has a head 244 attached to the free end thereof. A high conductivity member 246 fits within head 244 and is part of active face 218. A temperature probe 248 is mounted within member 246 to measure the temperature of the fluid whose shear stress is being measured. Leads 250 extend from the temperature probbe to a suitable measurement device.

In addition to the normal proximity probes (not shown) as illustrated in the previous embodiments, the displacement probe 252 is mounted near the reactive end of the lever to measure total axial force on the lever.

As has been previously noted, in application involving high pressures, the diaphragm embodiment shown in FIGS. 3 and 6 is often the preferred one. However, if the shear stress to be measured is low, so that the transducer must be relatively compliant to provide a suitable level of output signal, but the pressure and/or rheological normal force acting on the active face and/or on the lower surface of the diaphragm is high, the resulting axial deflection of the lever may be sufficiently high to interfere with proper operation of the transducer. In this instance, one can combine certain features of the embodiments shown in FIGS. 1 and 3. In particular, the basic configuration shown in FIG. 1 can be used in which the torsion bars are rectangular in cross section, being thicker in the axial direction. In this way, the torsion bars can be compliant with respect to torsion (shear load on the active face) but rigid with respect to shear (axial loading of the lever assembly). To prevent the flow of fluid into the upper portion of the body, a diaphragm can be inserted just below the member comprising the inner and outer rings and the torsion bars. By clamping this diaphragm around the lever and at the outer ring, the fluid is prevented from penetrating into the upper portion of the body. The diaphragm should be sufficiently thin so that it does not make a significant contribution to the torsional stiffness or rigidity of the torsion bars in response to the shear force on the active face. At the same time, if the slots or spaces between the inner and outer rings are sufficiently narrow, the diaphragm will still be able to withstand relatively high pressures.

It will be understood that the above described embodiments are for purposes of illustration only and changes and modifications may be made thereto without departing from the spirit and scope of the invention.

I claim:

1. An apparatus for measuring shear stress of a fluid, said apparatus comprising a substantially rigid lever, said lever having an active arm, a reactive arm, and a center section intermediate said active and reactive arms, an active face on said active arm forming a shear stress measurement surface, a housing at least partially surrounding said lever, said center section being secured to said housing by an elastic connecting portion comprising an inner ring and an outer ring, said outer ring being secured to said housing, said inner ring being secured to said center section, and at least one torsion bar connecting said inner and outer rings.

2. An apparatus for measuring shear stress of a fluid, said apparatus comprising a substantially rigid lever, said lever having an active arm, a reactive arm, and a center section intermediate said active and reactive arms, an active face on said active arm forming the shearing stress measurement surface, a housing at least partially surrounding said lever, said center section being secured to said housing by an elastic connecting portion comprising an outer ring secured to said housing, and a diaphragm extending between said outer ring and said center section, said diaphragm being deformed when a shear stress acts on said active face of said active arm.

3. An apparatus as defined in claim 1 or 2 wherein said active arm, said reactive arm, said center section and said elastic connection portion are formed of a single piece of material.

4. An apparatus as defined in claim 1 wherein said torsion bars have a generally rectangular cross-sectional configuration.

5. An apparatus as defined in claim 4 further including a sealing diaphragm extending between said housing and said lever to thereby prevent fluid from penetrating to the area about said reactive arm.

6. An apparatus as defined in claim 4 or 6 wherein said inner ring is connected to said center section by a plurality of said torsion bars, each of said torsion bars having a larger dimension in the axial direction to thereby be compliant with respect to shear load on said active face and more rigid with respect to axial loading of the lever.

7. An apparatus as defined in claim 1 or 2 wherein said means for measuring the movement of the reactive arm comprises a proximity probe mounted proximate the free end of the reactive arm to measure movement thereof.

8. An apparatus as defined in claim 1 or 2, wherein said means for measuring the movement of the reactive arm comprise first and second proximity probes, the first proximity probe being adapted to measure movement of the reactive arm in a first direction, the second proximity probe being adapted to measure movement of the reactive arm in a second direction which is normal to the first direction.

9. An apparatus as defined in claim 1 or 2 wherein said means for measuring the movement of the reactive arm comprises at least one proximity probe mounted proximate the free end of the reactive arm to measure movement thereof and the apparatus additionally including means for measuring movement of the reactive arm in the axial direction thereof.

10. An apparatus as defined in claim 1 or 2 wherein said active face has a generally circular configuration, said active face being adapted to be mounted in a cylindrical barrel, said active face having the curvature matching the curvature of the interior surface of the barrel.

11. An apparatus as defined in claim 2 further including a purge channel, said purge channel extending between a cavity formed in said housing about said active arm and the exterior to permit egress of fluid from said cavity.

12. An apparatus as defined in claim 1 or 2 wherein the ratio of length of the reactive arm to the length of the active arm is between about 2:1 to about 1:1.

13. An apparatus as defined in claim 1 or 2, further including temperature sensing means, said temperature sensing means including a temperature probe mounted interiorly of said active arm to measure the temperature of the fluid proximate the active face.

14. A method of measuring shear stress in a viscous or visco-elastic liquid comprising the steps of providing a shear stress transducer having a substantially rigid lever, the rigid lever formed of an active arm, a reactive arm and a center section intermediate said active and reactive arms, and active face on said active arm, a housing at least partially surrounding said lever, said center section being secured to said housing by an elastic connecting portion, mounting said transducer on a wall bounding the flow of said liquid such that said active face is substantially co-extensive with the wall, flowing said liquid past said active face in a direction substantially parallel thereto, and measuring the movement adjacent the free end of said reactive arm.

* * * * *